United States Patent [19]
Ueno et al.

[11] Patent Number: 5,109,120
[45] Date of Patent: Apr. 28, 1992

[54] REDUCTION OF CHEMICALLY MODIFIED PROTEINS

[75] Inventors: Hayao Ueno, Suita; Masahiko Fujino, Takarazuka, both of Japan

[73] Assignee: Takeda Chemical Industries, Ltd., Osaka, Japan

[21] Appl. No.: 364,707

[22] Filed: Jun. 9, 1989

Related U.S. Application Data

[62] Division of Ser. No. 21,768, Mar. 4, 1987, abandoned.

[30] Foreign Application Priority Data

Mar. 10, 1986 [JP] Japan .................. 61-53061

[51] Int. Cl.$^5$ .......... C07K 1/00; C07K 1/06; C07K 17/00; C12N 11/00
[52] U.S. Cl. ............ 530/351; 530/300; 530/303; 530/324; 530/345; 530/350; 530/387.1; 530/399; 530/402; 530/403; 530/391.1; 435/188
[58] Field of Search .......... 530/405, 409, 351, 815, 530/402, 403, 300, 345, 350, 391, 399, 303, 324, 387, 389; 435/188

[56] References Cited

U.S. PATENT DOCUMENTS

| | | | |
|---|---|---|---|
| 4,002,531 | 1/1977 | Royer | 195/68 |
| 4,179,337 | 12/1979 | Davis et al. | 435/181 |
| 4,261,973 | 4/1981 | Lee et al. | 424/78 |
| 4,275,000 | 1/1981 | Ross | 424/87 |
| 4,460,560 | 7/1984 | Tokes et al. | 424/1.1 |
| 4,525,339 | 6/1985 | Behl et al. | 424/16 |
| 4,609,546 | 9/1986 | Hiratani | 424/83 |

FOREIGN PATENT DOCUMENTS

| | | |
|---|---|---|
| 0043980 | 1/1982 | European Pat. Off. |
| 98110 | 1/1984 | European Pat. Off. |
| 0154316 | 9/1985 | European Pat. Off. |
| 154316 | 9/1985 | European Pat. Off. |
| 146472 | 4/1977 | United Kingdom |
| 2079291 | 1/1982 | United Kingdom |

OTHER PUBLICATIONS

Veronese et al., J. Pharm. Pharmacol. vol. 35, pp. 757-8 (1983).
Abuchowski et al., J. Biol. Chem. 252:3578 (1977).
Takahashi et al., Biochem. & Biophys. Comm. 121:261 (1984).
Nureddin, et al., J. Biochem. 147:71 (1975).
Slotboom et al., Biochemistry, 14:5394 (1975).
Vik, et al., Int. Arch. Allergy Immun. 74:55 (1984).
King, et al., Int. Arch. Allergy Immun. 60:439 (1981).

*Primary Examiner*—F. T. Moezie
*Assistant Examiner*—Andrew Rozycki
*Attorney, Agent, or Firm*—David G. Conlin; Ronald I. Eisenstein

[57] ABSTRACT

The invention provides chemically modified proteins having a group of the formula:

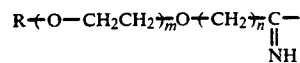

wherein R represents a hydrogen atom or a lower alkyl, m represents an optional positive integer and n represents an integer 1 to 4, the group being bonded to at least one primary amino group of the protein, and a method of producing the same. The chemically modified proteins according to the invention can be produced by reacting a protein with an imidoester of the formula:

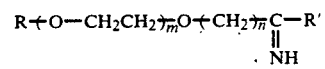

wherein R, n and m are as defined above, R' represents a group constituting an imidoester with an adjacent imidoyl group. The chemically modified proteins according to the invention are useful as drugs, among others.

13 Claims, 2 Drawing Sheets

REDUCTION OF CHEMICALLY MODIFIED PROTEINS

This is a divisional of application Ser. No. 021,768, filed on Mar. 4, 1987, now abandoned.

BACKGROUND OF THE INVENTION

1. Field of the Invention

The present invention relates to a biologically active protein having extended blood-circulation life or reduced immunogenicity and to a method of production thereof.

2. Description of the Prior Art

Biologically active proteins are expected to be used as effective drugs. Progress of gene recombination technology has recently allowed the production of such proteins on a large scale. In some cases, however, the biological activity of a protein administered to a living body remains effective only for a short time, due to its extremely rapid elimination in the circulation. In addition, administration of biologically active protein obtained from organisms other than human, such as microorganisms or animals, to human, may result in critical symptoms due to the immune reaction Therefore, technology development is desired which delays the rate of elimination of the protein from the body and which further reduces immunogenicity (antigenicity) thereof while activity is retained.

For the purpose of reducing the rate of elimination and immunogenicity, there is a method of modifying biologically active proteins with polyethylene glycol.

Polyethylene glycol itself is poorly antigenic, and when combined with an immunogenic protein, it is known to reduce the immunogenicity of the protein. Proteins modified with polyethylene glycol are said to be enhanced in blood-circulation life, and thus to maintain biological activity for a longer time. Means available for coupling polyethylene glycol to a protein include a method using polyethylene glycol methylether and cyanuric chloride (or fluoride) and a method using carboxyl derivatives of polyethylene glycol. As the former requires a relatively high, alkaline pH at the reaction, it cannot be applied to biologically active proteins which will be inactivated under alkaline conditions. Moreover, the toxicity of cyanuric chloride itself is troublesome. In the latter, coupling agents such as carbodiimide may cause inter- or intra-molecular cross-linking of the protein, and, furthermore, the destruction of the active conformation of protein may occur due to neutralization of the positively charged groups on the protein by the reaction. In another method, where either alkyl- or alkanoyl-polyethylene glycol aldehyde is introduced into biologically active protein in the presence of a boronic reducing agent, the reducing agent may break the disulfide bond related to the maintenance of the active conformation of protein, and may decrease the biological activity of the protein and insolubilize the protein by changing higher order structure.

SUMMARY OF THE INVENTION

While working to improve the conventional methods described above, the inventors have now found that the rate of elimination of a biologically active protein from blood-circulation can be reduced by chemically modifying at least one amino groups of the protein with an imidoyl group delineated by the formula:

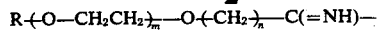

wherein, R represents a hydrogen atom or a lower alkyl, m represents an optional positive integral number and n represents an integer 1 to 4.

Further studies based on this finding, resulted in the developement of the present invention.

The present invention relates to:

(1) a chemically-modified protein having an imidoyl group of the formula:

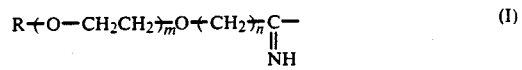

wherein R represents a hydrogen atom or a lower alkyl, m represents an optional positive integer and n represents an integer 1 to 4, the group being bonded to at least one primary amino group of the protein, (2) a method for producing a chemically-modified protein having an imidoyl group delineated by formula (I), the group being bonded to at least one primary amino group of the protein, which comprises reacting a protein with an imidoester of the formula:

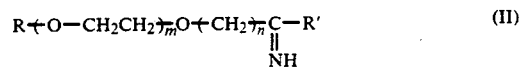

wherein R, m and n have the same meaning as in the previous formula (I), R' constitutes an imidoester group with an adjacent imidoyl group or a salt thereof, and (3) a compound delineated by the formula II or a salt thereof.

Proteins which can be used as raw materials in the present invention include those having biological activity; natural proteins derived from animals including humans, from microorganisms or from plants, proteins produced by genetic engineering and synthesized protein can be all used as long as they are biologically active. For example, cytokines such as interferons [interferon-α(IFN-α), interferon-β (IFN-β) and interferon-γ (IFN-γ)]and interleukin-2 (IL-2); hormones such as growth hormones and insulin; enzymes such as urokinase, superoxide dismutase (SOD) and asparaginase; and other proteins such as immunoglobulins, trypsin inhibitors, all kinds of proteases and peptidases, all kinds of cytochromes, islet-activating proteins (IAPs), all kinds of inhibitor proteins and neocarzinostatin, can be used. Preferred among such biologically active proteins are various IFNs (rIFN-α, rIFN-β, rIFN-γ) and rIL-2 produced by gene recombination techniques, SOD derived from animals or from microorganisms, and the like.

These proteins preferably have a molecular weight of approx. 5,000 to 50,000, especially preferably 10,000 to 30,000.

The primary amino groups of the proteins include N-terminal amino group and ξ-amino groups of lysine residues.

A lower alkyl represented by R in the above formulas (I) and (II) preferably has 1 to 18 carbon atoms. Such alkyls include methyl, ethyl, n-propyl, i-propyl, n-butyl, i-butyl, sec-butyl, t-butyl, n-pentyl, isopentyl, n-hexyl, isohexyl, n-heptyl, isoheptyl, n-octyl, isooctyl, n-nonyl, isononyl, n-decyl, isodecyl, n-undecyl, n-dodecyl, n-tridecyl, n-tetradecyl, n-pentadecyl, n-hexadecyl, n-heptadecyl and n-octadecyl. Those having 1 to 4 carbon atoms are especially preferred.

The optional positive integer represented by m in the said formulas is preferably 500 or less, more preferably 7 to 150.

The number represented by n in the said formulas is especially preferably 2 or 3.

The group of formula (I) preferably has a molecular weight of 25,000 or less, more preferably about 350 to 7,000.

The residue R' in formula (II) which constitutes an imidoester with an adjacent imidoyl group, include groups of the formula;

—OR"

wherein, R" represents an alkyl, an aryl, or an aralkyl.

The alkyls represented by R" in the above formula preferably has 1 to 8 carbon atoms. Such alkyls include methyl, ethyl, n-propyl, i-propyl, n-butyl, i-butyl, sec-butyl, t-butyl, n-pentyl, n-hexyl, n-heptyl and n-octyl. Those having 1 to 4 carbon atoms are especially preferred.

The alkyl may have one or two substituent(s) of chlorine or fluorine.

The aryls represented by R" include unsubstituted phenyls and phenyls having one or two alkyl(s) of 1 to 3 carbon atoms (e.g. methyl, ethyl, propyl, etc.) as substituent(s).

The aralkyls represented by R" include benzyl, phenethyl and phenylpropyl.

The chemically-modified protein of the present invention can be produced by reacting protein, for example, biologically active protein and an imidoester expressed by formula (II).

Salts delineated by the formula:

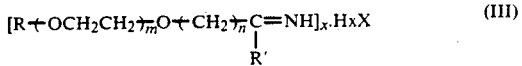
(III)

can also be used in place of imido esters expressed by formula (II). (In the formula, R, R', m and n have the same meaning as above. x represents a positive integer.

In salts expressed by formula (III), HxX is an acid of which HCl, CF$_3$COOH, HClO$_4$, H$_2$SO$_4$, CH$_3$COOH, CCl$_3$COOH, H$_3$PO$_4$, etc. are preferred.

When a biologically active protein is modified using compounds (II) or (III), the molar ratio of the compound to the protein can be chosen from the range of approx. 1:1 to 10,000:1. The degree of modification can be optionally chosen by changing either the molar ratio of the protein/compounds (II) or (III), or the concentrations of the protein and compound (II) or (III) in the reaction mixture. Any solvent can be used as long as it does not disturb the reaction and does not inactivate the protein. For example, water, a phosphate buffer, a borate buffer, a Tris buffer and an acetate buffer can be used. An organic solvent which does not inactivate the protein and does not disturb the reaction, such as a lower alkanol (e.g. methanol, ethanol, i-propanol), acetonitrile, dimethyl sulfoxide or dimethylformamide, may also be employed. In addition, compound (II) or (III) can be added to the reaction mixture directly or after dissolution in either a buffer or an organic solvent as long as the solvent neither disturbs the reaction nor inactivates the protein. It does not matter whether the protein or compound (II) or (III) is first added to the reaction media; simultaneous addition of the protein and compound (II) or (III) is also permitted. The reaction pH can be chosen from a wide range, approx. 3 to 14, but slightly alkaline conditions (approx. pH 7 to 9) is preferable. In addition, the degree of modification of the biologically active protein can be changed by varying the reaction pH. The reaction temperature may be selected within the range in which denaturation of the protein does not occur, but is preferably between approx. 0° and 40° C. A reaction time of approx. 0.5 to 72 hours, generally 3 to 30 hours, will be sufficient for the reaction. The desired, chemically-modified protein can be obtained by purifying the reaction mixture by conventional methods for purifying proteins such as dialysis, salting-out, ultra filtration, ion exchange chromatography, gel filtration, high performance liquid chromatography or electrophoresis. The degree of modification of amino groups can be calculated, for example, by amino acid analysis after acid hydrolysis.

Imidoester (III) can be synthesized from poly ethylene glycol derivatives delineated by the formula:

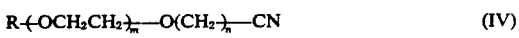
(IV)

wherein R, m and n have the same meanings as above. The following process for the production thereof is simple and preferable.

Thus, the compound (IV) is first dissolved in a dehydrated lower alkanol (HO-R', wherein R' has the same meaning as defined above.). The alkanol solution blown with anhydrous acids (e.g. dry hydrogen chloride) is left at about −70° C. to +30° C., preferably at approx. −20° C. The resulting reaction mixture can be purified using ordinary chemical methods such as concentration, reprecipitation, recrystallization or the like. Thus obtained compound (III) can be stored for a long time under desiccated conditions at low temperature, preferably in a refrigerator or freezer. Compound (II) can be obtained by treating compound (III) with an alkaline compound, e.g. sodium hydroxide or potassium hydroxide.

Polyethylene glycol derivative (IV) can be obtained by the following methods; Polyethylene glycol derivative (IV) (n=3) can be obtained by treatment of the compound of the formula:

(V)

wherein R and have the same meaning as above, except that R does not include hydrogen, with Na, NaH, K or an alkoxide of Na, K etc., followed by adding bromobutylonitrile [Br(CH$_2$)$_3$ CN]; Compound (IV) (n=2) can be obtained by dropping acrylonitrile into compound (V) treated with a small amount of NaH in an inert solvent, such as benzene. In both cases, the reaction mixture can be purified using ordinary chemical processes such as extraction, concentration, recrystallization, reprecipitation, chromatography or distillation.

The chemically-modified protein of the present invention has the group of formula (I) directly bonded to at least some primary amino groups of the biologically active protein.

The groups of formula (I) should have a molecular weight corresponding to aprox. 1 to 10%, more preferably approx. 2 to 8% of the molecular weight of the modified protein.

When the raw protein has amino groups only at its N-terminus, the chemically-modified protein obtained according to the present invention has a group of formula (I) directly bonded to said amino groups. When the biologically active protein has one or more lysine molecules, the modified protein has the group of formula (I) directly bonded to some of their ξ-amino groups, preferably appox. 5 to 80% (average), particularly approx. 10 to 50% (average) of the ξ-amino groups. In this case, the N-terminal amino group may have or may not have the group of formula (I) directly bonded to it.

The chemically-modified protein of the present invention has a useful biological activity similar to that of the corresponding unmodified physiologically active protein and thus may be used in drugs, etc.

Compared to the corresponding known unmodified biologically active protein, the present chemically-modified protein has a reduced rate of elimination from the circulation of a living body, thus remaining effective for a longer period, and also lower toxicity and antigenicity. Accordingly, it can be used safely for the same purpose and in the same way as well-known biologically active proteins.

The present chemically-modified protein can be administered orally or parenterally to mammals (e.g. monkey, dog, pig, rabbit, mouse, rat, human, etc.) in the form of suitable pharmaceutical compositions (e.g. capsules, injection, etc.) with the conventional carriers, diluents, etc.

For example, the chemically-modified rIL-2 of the present invention can be used as a preventive or therapeutic agent for tumors; it is administered at a dose similar to that with unmodified rIL-2, i.e. in very small amounts in the form of an injection, capsules, etc.

The chemically-modified rIFN-γ of the present invention, when used as agent for antiviral effect, antitumor effect, cellular growth inhibition, or immunopotentiating activity, is administered to human adults at a dose of $1.0 \times 10^5$ to $1.0 \times 10^8$ unit/day by intravenous or intramuscular injection, etc.

The chemically-modified rIFN-αA of the present invention, when used as a therapeutic agent for its antitumor effect or antiviral effect, may be administered to patients in approx. $1.0 \times 10^5$ to $1.0 \times 10^6$ unit/day as amount of rIFN-αA by injection.

The chemically-modified SOD of the present invention, when used as an antiinflammatory agent, may be administered in 1 to 5 mg/kg/day as amount of SOD in the form of an injection, tablets, etc. to an animal The compounds (II) and (III) can be used as a raw material or a starting material for the production of the present chemically modified protein having the group (I).

In the present specification, amino acids, in some cases, are represented by abbreviations based on the IUPAC-IUB Nomenclature (established by the Commission of Biochemical Nomenclature), for example:

Lys: Lysine

EXAMPLES OF THE PREFERRED EMBODIMENT

Figure 1:
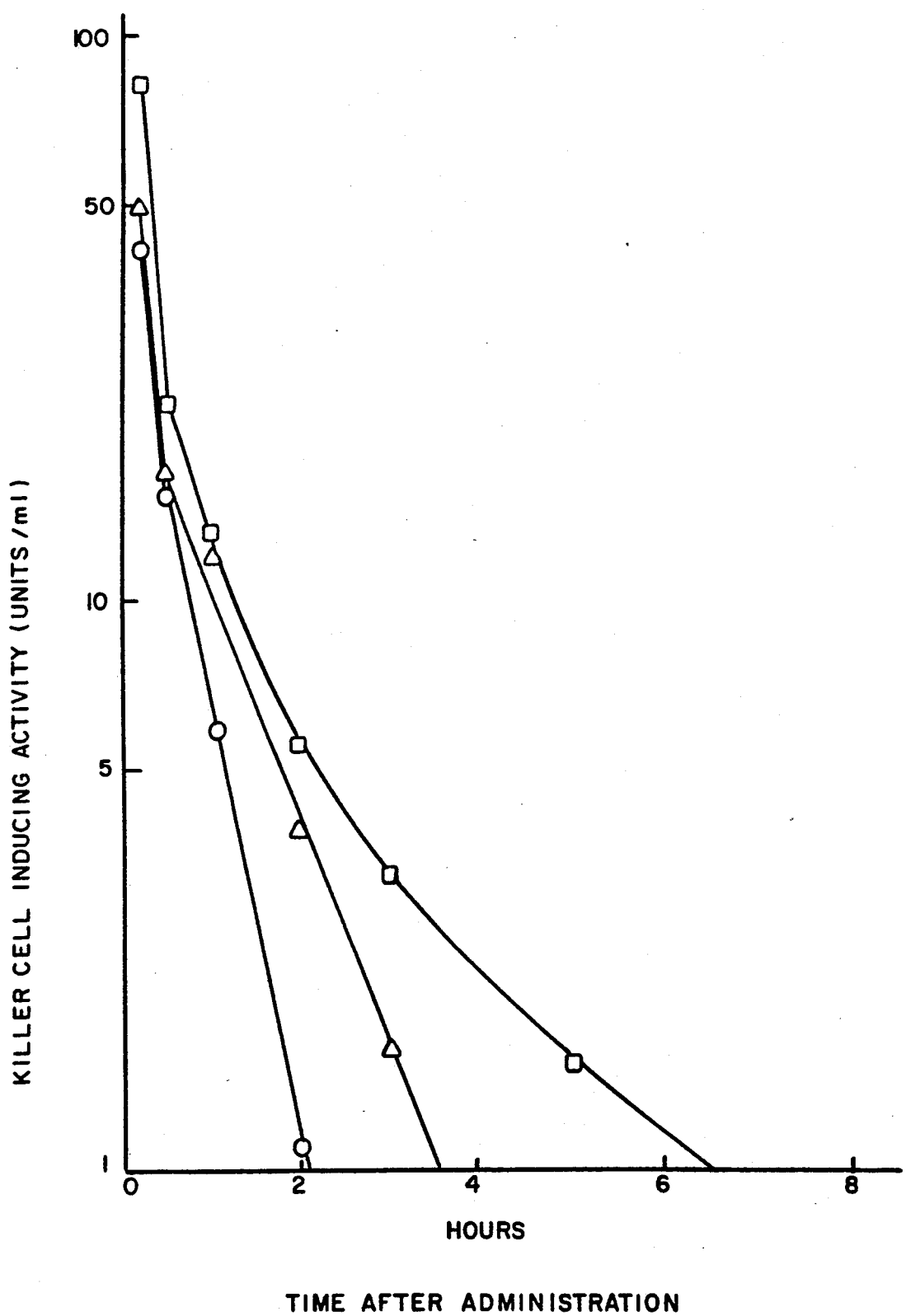
FIG. 1 shows the activity-sustaining effect of the modified proteins in rat blood plasma, as described in Example 1 (iv).

The present invention is hereinafter described in more detail with one reference example and some working examples of its preferred embodiment.

REFERENCE EXAMPLE 1

Synthesis of polyethylene glycol imido ester

Three grams of polyethylene glycol monomethylether mono-β-cyanoethylether synthesized from polyethylene glycol monomethylether having an average molecular weight of 350 was dissolved in 3 ml of anhydrous methanol. To the resulting solution, dry hydrogen chloride was blown at −20° C. to saturation concentration, and the reaction vessel was sealed and left in a freezer for 3 days. After anhydrous ether was added, the solution was cooled again in the freezer. Four hours later, the upper ether layer was decanted; anhydrous ether was added again to the remaining solution. The solution, after being stirred well, was allowed to stand in a freezer, yielding solid product about 1 hour later. After the ether was removed, the solid product was washed well with anhydrous ether and cooled in the freezer. After the solid product had settled, the ether layer was decanted. This process was repeated twice more for thorough washing of solid product. The solid product was dried under reduced pressure in a desiccator containing both phosphorus pentoxide and solid NaOH for 1 hour, yielding imidoester of polyethylene glycol monomethylether having an average molecular weight of 350 (its actual molecular weight is greater than 350 by the weight of

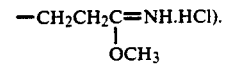

This product is a syrupy liquid at room temperature. A triplet corresponding to

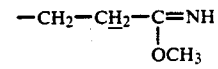

was detected at the position of δ=2.3 in $^1$H-NMR spectrum (in $d_6$-DMSO, 90 MHz) of the product. Absorption corresponding to -CN disappeared in IR spectrum of the product.

The product was subdivided and sealed in some small containers and stored in a freezer.

Polyethylene glycol mono-β-cyanoethylethers synthesized from polyethylene glycol monomethylethers having average molecular weights of 550, 750, 1,900, and 5,000, respectively, were subjected to the same treatment as above, yielding corresponding imidoester of polyethylene glycol monomethylether.

EXAMPLE 1

Modification of interleukin-2

(i) Four mg of interleukin-2 (rIL-2), which is obtained by employing *Escherichia coli* DH1/pTF4 (IFO 14299, FERM BP-629) via the method described in Japanese Patent Publication (Unexamined) No.115528/85 or European Patent Publication No. 145,390 was dissolved in 2 ml of 25 mM phosphate buffer solution (pH 7.6) and cooled with ice. With stirring under ice cooling, the resulting solution was added to 17 mg of the imidoester of polyethylene glycol monomethylether (average molecular weight: 550) obtained in Reference Example 1, and then the pH of the reaction mixture was immediately re-adjusted to 7.6 using 0.2N NaOH and reacted for 5 hours. The resulting reaction mixture was applied to a column (0.9×50 cm) packed with Sephadex G-25 (Pharmacia AB, Sweden) equilibrated with 25 mM ammonium acetate (pH 6.0), and eluted with the same buffer with monitoring absorption at 280 nm wavelength, yielding approx. 8 ml of a main fraction. The recovery rate of the protein was 60%. Three ml of the fraction, after lyophilization, was hydrolyzed with 6N hydrochloric acid at 110° C. in a sealed degassed tube for 24 hours, after that it was subjected to amino acid analysis. The analysis data showed that 2.8 of the eleven Lys residues of rIL-2 had been modified with polyethylene glycol imidoester.

(ii) In the same manner as stated in (i), 24 mg and 57 mg of polyethylene glycol imidoesters obtained by the procedures shown in Reference Example 1 from polyethylene glycol monomethylethers having average molecular weights of 750 and 1,900, respectively, were each added to rIL-2. The amino acid analysis of the reaction product showed that 2.9 and 2.0 of the eleven Lys residues of rIL-2 had been modified with polyethylene glycol imidoesters, respectively.

(iii) Measurements of natural killer (NK) cell inducing activity of the three rIL-2s modified with polyethylene glycol imidoester, obtained in (i) and (ii) gave the values 14,900, 16,500, and 7,180 unit/ml, respectively.

(iv) Approx. 3 mg of each of unmodified rIL-2 and the two rIL-2s modified with polyethylene glycol ester, obtained in (ii), was intravenously administered to rats to measured its biological activity in blood plasma. The following was found: NK cell inducing activity in blood plasma, observed in rats receiving modified rIL-2, remained effective for a longer period than that observed in rats receiving unmodified rIL-2. Lasting of the activity tended to increase with the increase in molecular weight of polyethylene glycol.

The results obtained in the measurements are shown in FIG. 1.

In FIG. 1, -△- and -□- show chemically-modified rIL-2s of the present invention, obtained in (ii). More specifically, -△-, -□-, and -○- show the time-course of killer cell inducing activities in blood plasma after injection of the modified rIL-2 obtained from polyethylene glycol imidoester having an average molecular weight of 750, of the modified rIL-2 obtained from polyethylene glycol imidoester having an average molecular weight of 1,900, and of the unmodified rIL-2 used as a control, respectively.

EXAMPLE 2

Modification of interferon-γ(rIFN-γ)

(i) Three ml of rIFN-γ solution (approx. 1.7 mg/ml), obtained by employing *Escherichia coli* 294/pHIT trp 2101 to produce rIFN-γ and by purifying with the use of anti-IFN-γ antibody produced by Mouse B hybridoma gamma 2-11.1 (deposited at C.N.C.M. of Institute Pasteur, France under the deposit number of I-242) via the method described in European Patent Publication No. 110044 or Japanese Patent Publication (unexamined) No. 186995/84, was applied to a column packed with Sephadex G-25 equilibrated with a 20 mM phosphate buffer (pH 7.5) containing 10 mM N-acetylcystein and eluted with the same buffer, yielding approx. 4.5 ml of a main protein fraction. With stirring under ice cooling, the resulting IFN-γ fraction was added to 50 mg of imidoester of polyethylene glycol monomethylether (average molecular weight: 750), obtained in Reference Example 1, after that pH of the reaction mixture was immediately re-adjusted to 7.5 using a saturated NaHCO$_3$ solution. The resulting solution was stirred in a ice bath for more than 4 hours and then stand overnight in a refrigerator. Approx. 3 ml of the supernatant, after removing the resulting precipitates by centrifugation, was applied to a column (1.2 ×45 cm) packed with Sephadex G-75 equilibrated with a 25 mM ammonium acetate buffer solution (pH 6.0) for elution, yielding approx. 5 ml of a main fraction. Reduced form glutathione was added to the fraction to a concentration of 10 mM, yielding a solution containing rIFN-γ modified with polyethylene glycol imidoester. The measurement of rIFN-γ activity (Enzyme-Immunoassay method: EIA method) and antiviral activity of the resulting solution showed the value of $3.4 \times 10^4$ ng rIFN-γ/ml and $2.31 \times 10^4$ IU/ml, respectively. Part of the supernatant described above was passed through a column (0.9×50 cm) packed with Sephadex G-75 equilibrated with 0.1M acetic acid, yielding a protein fraction. After lyophilization, the protein fraction was hydrolyzed with 6N HCl at 110° C. in a sealed degassed tube for 24 hours and followed by amino acid analysis. Approx. seven of the twenty Lys residues of the rIFN-γ were found to have been modified.

(ii) One-hundred mg of imidoester of polyethylene glycol monomethyl ether (average molecular weight: 1,900), obtained in Reference Example 1, and rIFN-γ were treated in the same manner as stated in (i), yielding rIFN-γ modified with polyethylene glycol imidoester. Its rIFN-γ activity (EIA method) and antiviral activity were $3.6 \times 10^4$ ng rIFN-γ /ml and $7.7 \times 10^3$ IU/ml, respectively. Amino acid analysis showed that approx. two of the twenty Lys residues of the rIFN-γ had been modified.

(iii) Unmodified rIFN-γ and modified rIFN-γ s obtained in (i) and (ii) were each intravenously administered to rats at doses of $7.90 \times 10^4$, $4.62 \times 10^3$, and $1.54 \times 10^3$ IU, respectively. rIFN-γ activities in blood plasma were then measured by EIA method, proving that the rIFN-γ s modified with polyethylene glycol imidoester were clearly slower in elimination than the unmodified one.

Figure 2:
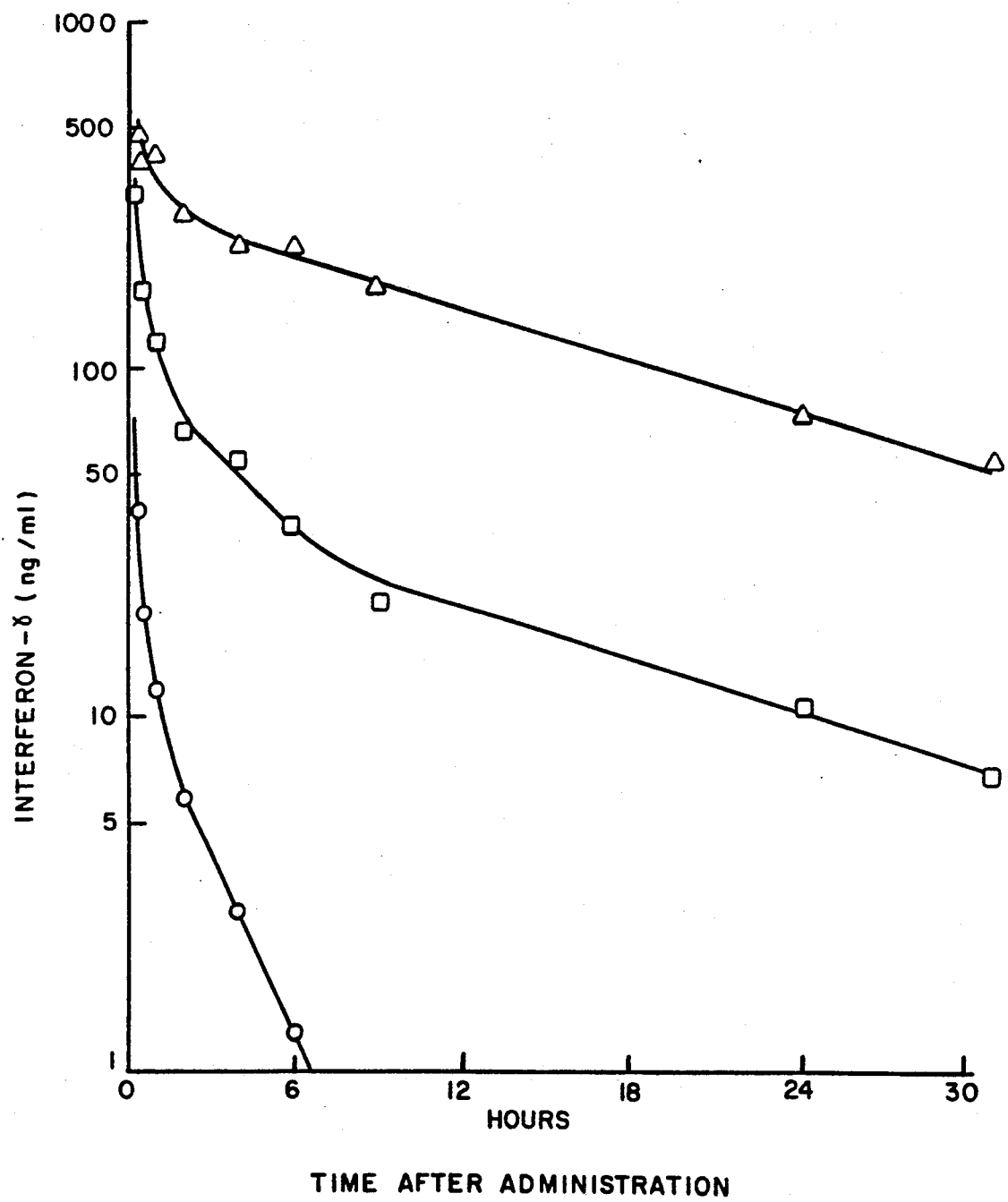
FIG. 2 shows the eliminate-retarding effect of the modified proteins in rat blood plasma, as described in Example 2 (iii).

Results obtained in the measurements are shown in FIG. 2; -□-, -△-, and -○- show time course of changes in plasma rIFN-γ activities after injection of the modified rIFN-γs obtained in (i) and (ii) and of the unmodified rIFN-γ used as a control, respectively.

EXAMPLE 3

Modification of interferon-αA (rIFN-αA)

(i) Five ml of rIFN-α A solution (containing approx. 4 mg protein) obtained via the method described in Japanese Patent Publication (unexamined) No..79897/1982 or European Patent Publication No.43,980 was dialyzed overnight against 0.05M phosphate buffer (pH 7.0). To the retentate, 250 mg of the imidoester of polyethylene glycol monomethylether (average molecular weight: 5,000), obtained in Reference Example 1, was added with stirring under ice cooling, after that the pH of the solution was immediately adjusted to 7.5 using 0.2 N NaOH. After stirring for 3.5 hours, the reaction mixture was then applied to a column (0.9×50 cm) packed with Sephadex G-75 equilibrated with a 25 mM ammonium acetate buffer solution (pH 6.0) and eluted with the same buffer, yielding a main protein fraction. The resulting fraction was then concentrated using Immersible CX-10 (Milipore Inc., USA), yielding approx. 17 ml of rIFN-αA modified with polyethylene glycol imidoester (protein content: 105 μg/ml). Amino acid analysis of the acid hydrolysate showed that 3.1 of the eleven Lys residues of the rIFN-αA had been modified. Product activity was found to be 3.0×10⁷ IU/ml (EIA method).

(ii) rIFNαA was treated with 100 mg of imidoester of polyethylene glycol monomethylether (average molecular weight: 750), obtained in Reference Example 1, in the same manner as stated in (i), yielding approx. 21 ml of solution containing rIFN-αA modified with polyethylene glycol imidoester (protein content: 107 μg/ml). Amino acid analysis of the product showed that 6.2 of the eleven Lys residues of the rIFN-αA had been modified. Activity measured by EIA method gave the value 7.21×10⁶ IU/ml.

When the modified rIFN-αAs obtained in (i) and (ii) were each administered to rats, obvious reduced clearance from blood was found.

EXAMPLE 4

Modification of superoxide dismutase (SOD)

(i) 5.5 mg of SOD obtained by employing *Serratia marcescens* ATCC 21074 via the method described in Agricultural and Biological Chemistry, 47, 1537 (1983), Japanese Patent Publication (unexamined) Nos. 29285/1982 and 16685/1983, European Patent Publications No. 45,222 and 70,656, was dissolved in 2 ml of 0.1 M borate buffer (pH 8.7). The resulting solution was reacted overnight with 165 mg of imidoester of polyethylene glycol monomethylether (average molecular weight: 5,000), obtained in Reference Example 1, at pH 8.5 in a cold room overnight. The resulting reaction mixture was then applied to a column (1.8 ×50 cm) packed with Sephadex G-100 and eluted with a 0.05M phosphate buffer (pH 7.0), yielding a main protein fraction, which was then concentrated, yielding approx. 16.5 ml of modified-SOD solution containing 0.282 mg/ml protein.

(ii) Serratia-deriving SOD obtained in (i) was added, for reaction, to 330 mg of polyethylene glycol monomethylether imidoester having the same molecular weight as above. The resulting reaction mixture was then treated in the same manner as stated in (i), yielding 22 ml of modified-SOD solution containing 0.226 mg/ml protein.

(iii) Five ml of each of the modified-SOD solutions obtained in (i) and (ii) was dialyzed overnight against distilled water Each resulting retentate, after lyophilization, was hydrolyzed with 6 N hydrochloric acid at 110° C. for 24 hours; 23% and 29% of the SOD Lys residues were found to have been modified, respectively.

(iv) Activity was compared between the modified SODs obtained in (i) and (ii) and unmodified SOD; the residual activity of the modified SOD obtained in (i) and that of the modified SOD obtained in (ii) were 65% and 60% of that of the unmodified SOD, respectively.

Both modified SODs obtained in (i) and (ii) were each found to be slower in elimination from blood and lower in antigenicity compared to unmodified SOD.

The following references, which are referred to for their disclosures at various points in this application, are incorporated herein by reference.

Japanese Patent Publication (Unexamined) No.115528/1985
European Patent Publication No. 145390
European Patent Publication No. 110044
Japanese Patent Publication (Unexamined) No.186995/1984
Japanese Patent Publication (Unexamined) No.79897/1982
European Patent Publication No. 43980
Agricultural and Biological Chemistry, 47 1537(1983)
Japanese Patent Publication (Unexamined) No.29285/1982
Japanese Patent Publication (Unexamined) No.16685/1983
European Patent Publication No. 45222
European Patent Publication No. 70656

What is claimed is:

1. A method of producing a chemically modified protein having imidoyl groups whose number is from one to the number of primary amino groups of the protein of the formula:

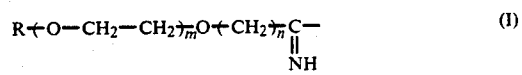

wherein R represents a hydrogen atom or an alkyl group having 1 to 18 carbon atoms, m represents a positive integer from 7 to 150 and n represents an integer 1 to 4, each group being bonded to one primary amino group of the protein, wherein the molecular weight of the group of the formula (I) is from 350 to 7,000, which comprises reacting a protein with an imidoester of the formula:

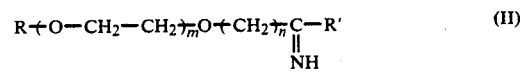

wherein R, m and n are as previously defined, R' represents a group of the formula: —OR″, wherein R″ represents a substituted or unsubstituted alkyl groups having 1 to 8 carbon atoms, wherein the substituents are one or two chloro or fluora, or a substituted or unsubstituted aralkyl group selected from the group consisting of benzyl, phenethye and phenylpropyl, wherein the substituents are one or two alkyl groups having 1 to 3 carbon atoms which forms an imidoester with the imidoyl group (I), or with an imidoester salt of the formula:

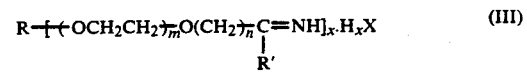

wherein R, R', m and n are as previously defined, x is an integer of 1-3 and HxX is an acid selected from the group consisting of HCl, H2SO4, CF3COOH, HClO4, CH3COOH, CCl3COOH, and H3PO4.

2. The method according to claim 1, wherein the protein is (1) a cytokine selected from the groups consisting of interferon-α, interferon-β, interferon-γ and interleukin-2, (2) a hormone selected from the group consisting of growth hormones and insulin, (3) an enzyme selected from the group consisting of urokinase, superoxide dismutase and asparaginase, or (4) a protein selected from the group consisting of immunoglobulins, islet-activating proteins, inhibitor proteins and neocarzinostatin.

3. The method according to claim 2, wherein the protein is an interferon selected from the group consisting of interferon-α, interferon-β and interferon-γ.

4. The method according to claim 3, wherein the protein is interferon-γ modified with an imidoester of polyethylene glycol monomethyl ether.

5. The method according to claim 2, wherein the protein is interleukin-2 modified with an imidoester of poyethylene glycol monomethyl ether.

6. The method according to claim 2, wherein the protein is superoxide dismutase modified with an imidoester of polyethylene glycol monomethyl ether.

7. The method according to claim 1, wherein the reaction is conducted at pH 7 to 9, and 0° C. to 40° C. for 0.5 to 72 hours.

8. The method according to claim 1, wherein R" is benzyl, phenethyl or phenylpropyl.

9. The method according to claim 1, wherein R is methyl, ethyl, n-propyl, iso-propyl, n-butyl, iso-butyl, sec-butyl, t-butyl, n-pentyl, iso-pentyl, n-hexyl, iso-hexyl, n-heptyl, iso-heptyl, n-octyl, iso-octyl, n-nonyl, iso-nonyl, n-decyl, iso-decyl, n-undecyl, n-dodecyl, n-tridecyl, n-tetradecyl, n-pentadecyl, n-hexadecyl, n-heptadecyl or n-octdecyl.

10. The method according to claim 1, wherein n is 2 or 3.

11. The method according to claim 1, wherein the primary amino group is N-terminal α-amino group or ξ-amino group of lysine residue in the protein.

12. The method according to claim 6, which has the group of formula (I) bonded to 5 to 80% of ξ-amino groups of lysine residue in the protein.

13. The method according to claim 1, wherein the group of formula (I) has molecular weight corresponding to 1 to 10% of the molecular weight of the modified protein.

* * * * *

UNITED STATES PATENT AND TRADEMARK OFFICE
CERTIFICATE OF CORRECTION

PATENT NO. : 5,109,120

DATED : April 28, 1992

INVENTOR(S) : Hayao UENO and Masahiko FUJINO

It is certified that error appears in the above-indentified patent and that said Letters Patent is hereby corrected as shown below:

Column 10, line 44, replace "phenethye" with --phenethyl--.

Column 12, line 12, replace "6" with --11--.

Signed and Sealed this

Twenty-fifth Day of January, 1994

Attest:

BRUCE LEHMAN

*Attesting Officer*  *Commissioner of Patents and Trademarks*